United States Patent
Wolfe

(10) Patent No.: US 6,256,530 B1
(45) Date of Patent: Jul. 3, 2001

(54) OPTICAL INSTRUMENT AND TECHNIQUE FOR CANCER DIAGNOSIS USING IN-VIVO FLUORESCENCE EMISSION OF TEST TISSUE

(75) Inventor: William L. Wolfe, Tucson, AZ (US)

(73) Assignee: Denvu, L.L.C., Tucson, AZ (US)

( * ) Notice: Subject to any disclaimer, the term of this patent is extended or adjusted under 35 U.S.C. 154(b) by 0 days.

(21) Appl. No.: 09/153,774

(22) Filed: Sep. 15, 1998

(51) Int. Cl.$^7$ .................................................. A61B 5/00
(52) U.S. Cl. ................................................................ 600/477
(58) Field of Search .................................... 600/476, 477, 600/478, 310; 356/433, 317, 318, 319, 435

(56) References Cited

U.S. PATENT DOCUMENTS

| | | |
|---|---|---|
| 5,062,431 | 11/1991 | Potter .................................. 128/665 |
| 5,106,387 | 4/1992 | Kittrell et al. ......................... 606/15 |
| 5,111,821 | 5/1992 | Potter .................................. 128/654 |
| 5,115,137 | 5/1992 | Anderson-Engels et al. .... 250/461.2 |
| 5,131,398 | 7/1992 | Alfano ................................ 128/665 |
| 5,328,488 | 7/1994 | Daikuzono . | 
| 5,421,337 | 6/1995 | Richards-Kortum et al. ........ 128/665 |
| 5,470,331 | 11/1995 | Daikuzono . |
| 5,590,660 | 1/1997 | Macaulay et al. .................... 128/664 |
| 5,612,540 | 3/1997 | Richards-Kortum et al. .... 250/461.2 |
| 5,647,368 | 7/1997 | Zeng et al. ............................ 128/665 |
| 5,769,792 | * 6/1998 | Palcic et al .......................... 600/477 |
| 6,026,319 | * 6/1998 | Hayashi ............................... 600/476 |

\* cited by examiner

*Primary Examiner*—Francis J. Jaworski
*Assistant Examiner*—Eleni Mantis Mercader
(74) *Attorney, Agent, or Firm*—Antonio R. Durando

(57) ABSTRACT

A hand-held, small, lightweight instrument is disclosed that contains a light source capable of producing radiant energy in the spectral range between approximately 370 and approximately 410 nm, and an optical direction system for irradiating a target tissue by producing an illuminated spot thereon. A collection system is provided for receiving and directing fluorescent emissions in the frequency range between 450 and 700 nm returned from the target area to a detector. A processing system is used to determine the state of the tissue by using at least two and up to five spectral bands, preferably each being larger than 45 nm. Pairs of ratios of fluorescent intensities are compared to identify cancerous cells. An alphanumeric, false-color image and/or audio signal is immediately provided to inform a user of the state of the tissue.

15 Claims, 5 Drawing Sheets

OPTICAL INSTRUMENT AND TECHNIQUE FOR CANCER DIAGNOSIS USING IN-VIVO FLUORESCENCE EMISSION OF TEST TISSUE

BACKGROUND OF THE INVENTION

1. Field of the Invention

This invention pertains in general to the detection of cancer in various types of human tissue and, more particularly, to a novel procedure and instrumentation for in-vivo detection of cancerous cells using fluorescence excitation in tissue that is optically accessible for examination.

2. Description of the Related Art

Several techniques and instruments have been described by investigators for the purpose of detecting cancerous cells. For example, U.S. Pat. No. 5,062,431 to Potter (1991) utilizes in-vivo fluorescence detection of abnormal tissue by irradiating a photosensitized diagnostic region simultaneously with at least two excitation wavelengths. Fluorescent light emitted from the diagnostic region is detected and a signal is generated relating to the intensity of the fluorescence. A difference signal between the two wavelengths is used to distinguish the fluorescence of normal tissue from that of diseased cells.

In U.S. Pat. No. 5,106,387 (1992), Kittrell et al. disclose a method for identifying atheromaterial in a vascular lumen for diagnosis of arterial or vascular obstructions. Diagnosis is accomplished by spectrally analyzing the return radiation with or without a reference spectrum. U.S. Pat. No. 5,115,137 to Andersson-Engels et al. (1992) describes a method for detecting atherosclerosis and blood disorders by utilizing fluorescence excitation at wavelengths less than 500 nm. The intensity of a plurality of wavelengths, at least two of which have substantially equal absorption by blood, is used to evaluate the character of the tissue being tested.

U.S. Pat. No. 5,131,398 to Alfano et al. (1992) describes diagnosis of cancerous cells by using a substantially monochromatic excitation light and two detection bands at about 340 and 440 nm of the fluorescent emissions. The ratio of the fluorescent intensities at the two wavelengths for normal tissue is then calculated and used as a reference for comparison for identifying cancerous tissue. The invention is based on the discovery that when tissue is excited with monochromatic light at wavelength of about 300 nm, the resulting native fluorescence spectrum over the region from about 320 nm to 600 nm in cancerous tissue is substantially different from that of either benign or healthy tissue. The patent further teaches that avoiding the use of fluorescent emissions between about 380 nm and 430 nm, one can ignore the effect on the fluorescence intensity resulting from blood absorption. In addition, the patent teaches that at excitation wavelengths above 315 nm the ratios of fluorescent-emission intensities are indistinguishable between cancerous and benign cells.

In spite of the progress illustrated by the prior art, it still remains difficult to identify cancerous tissue by direct in-vivo examination. The use of monochromatic or narrow bandwidth for excitation and emission light (such as the 20 nm bandwidth taught by Alfano et al.) requires sophisticated and expensive instrumentation capable of detecting very low light intensities and of functioning with low signal-to-noise ratios. Therefore, it would be very useful to devise a technique that allows the use of wideband radiation and reception and that produces visible light signals for manual operation of the detection instrument. The present invention is directed at providing such improvements to prior-art devices and procedures.

BRIEF SUMMARY OF THE INVENTION

It is a general object of this invention to provide a self-contained, manually-operated diagnostic instrument for the measurement of human-tissue surfaces to determine whether they are cancerous, precancerous or benign.

A further object of the invention is that such diagnostic instrument be simple and inexpensive, so that it can be used by primary care physicians.

It is a still further objective of the invention that the diagnostic instrument be convenient to use.

Yet another object is that such diagnostic instrument be noncontact and aseptic.

Also an object of the invention is that the instrument be capable of defining the area to be diagnosed unambiguously.

A related and essential goal of the invention is to develop a detection technique that makes it possible to implement these objectives with acceptable reliability.

Finally, an objective of the invention is a procedure and corresponding apparatus that are suitable for direct implementation using existing optical and electronic apparatus.

Therefore, according to these and other objectives, the present invention consists of a hand-held, gimbaled or tripod-mounted instrument that contains a light source capable of producing radiant energy in the spectral range between approximately 370 and approximately 410 nm, and an optical direction system for irradiating a target tissue by producing an illuminated spot thereon. A collection system is provided for receiving and directing fluorescent emissions returned from the target area to a detector. A processing system is used to determine the state of the tissue by using at least two and up to five spectral bands, preferably each being larger than 45 nm. Pairs of ratios of fluorescent intensities are compared to identify cancerous cells. An alphanumeric and/or audio signal is immediately provided to inform a user of the state of the tissue.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

DESCRIPTION OF THE PREFERRED EMBODIMENTS OF THE INVENTION

The heart of this invention lies in the recognition that by monitoring wider fluorescent-emission bandwidths than previously done more information is collected at each intensity measurement regarding differences between the emission spectra of cancerous and benign cells. In addition, stronger signals are generated that make it possible to implement the diagnostic technique of the invention with simpler and less expensive technology that can be incorporated in a self-contained, manually-operated device. Finally, this invention discloses a more versatile and discriminating approach for distinguishing the fluorescent emissions of cancerous cells from that of benign tumors and healthy tissue.

Figure 1:
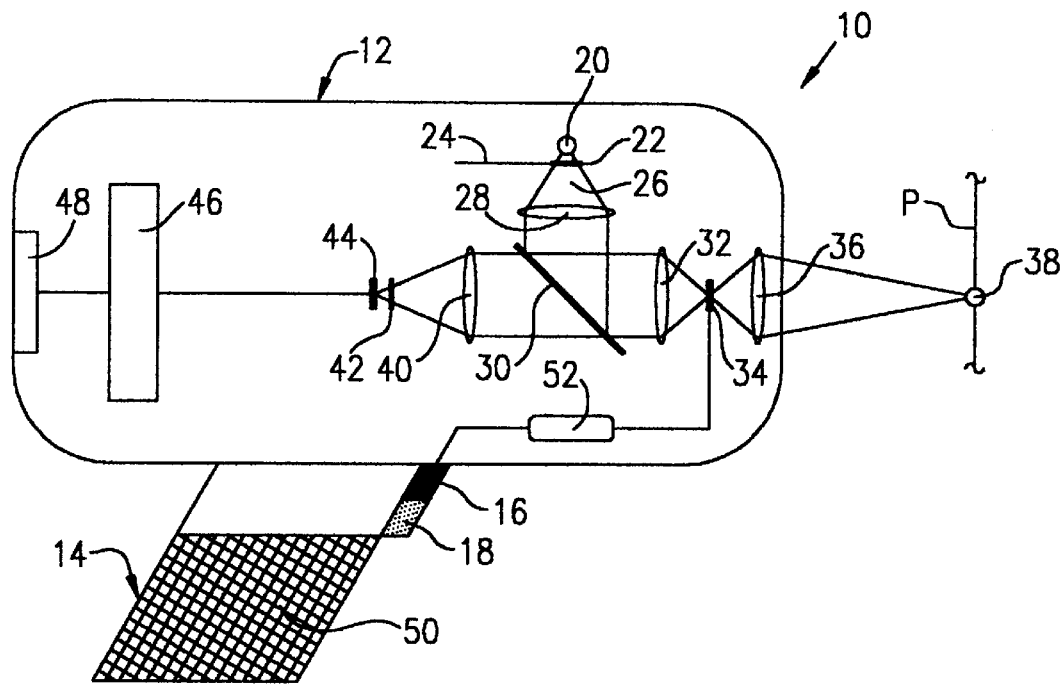
FIG. 1 is a schematic, elevational view of a manually-operated detection instrument according to the invention.

Referring to the drawings, wherein like reference numerals and symbols are used to identify like parts, FIG. 1 illustrates in schematic form a detection instrument 10 according to one embodiment of the invention. The drawing shows the functional components of the instrument 10 as they would appear in sectioned elevational view. This particular embodiment, which is designed for in-vivo diagnostic use, consists of a gun-type instrument comprising a housing 12 and a handle 14 with two finger controls or triggers 16 and 18. A light source 20 shines through a filter 22 mounted on a filter holder 24; the filtered light beam 26 is collimated by a lens 28 and reflected by a beam splitter 30 toward an adjustable-aperture arrangement that consists of a lens 32, an adjustable iris 34 and a refocussing lens 36. Thus, the light beam forms an approximately circular image or spot 38 on a target surface, such as the surface tissue of a patient P.

The light shining on the spot 38 excites a fluorescent emission that is returned to the same adjustable-aperture arrangement and passed through the beam splitter 30 toward a focusing lens 40, a filter set 42 and onto a detector 44. The electrical signals generated by the detector are sent to a microprocessor 46 that generates a message for a display unit 48 visible to a user of the instrument 10. The system is powered by batteries 50 contained in the handle 14. The two finger controls 16 and 18 in the handle are used to operate the instrument, as further detailed below.

As illustrated in FIG. 1, the diagnostic instrument 10 is preferably in the general shape of a pistol or gun with the housing 12 in the shape of a cylindrical barrel containing the optics and electronics and the handle 14 containing the batteries that constitute the power supply. The handle is designed to be conveniently gripped by the hand of a user and the entire structure is preferably made of a lightweight material. The electrical connections from the batteries to the microprocessor and to the controls are not shown, but are constructed and mounted according to well known standard techniques. The front end of the barrel may have a window (mounted in a traditional way) that is transparent to the excitation light and to the fluorescent light that is emitted from the area under investigation. Alternatively, the lens 36 may be used as a window. Obviously, the instrument 10 may be shaped in other convenient, ergonomic morphologies.

According to one aspect of the invention, the light source 20, the filter 22, the beamsplitter 30 and the set of filters 42 are chosen so as to produce light signals of selected wavelength and intensity on the detector 44. The selection is based on the concept of producing intensity information that can be used advantageously to discriminate between the fluorescent emissions of a cancerous tissue from those of a healthy one. I found that the use of broadband excitation light in conjunction with the judicious use of various kinds of ratios of signals received at different wavelengths of emitted fluorescent light can be determinative of the health state of the tissue under examination. For example, using excitation light with wavelength from 370 to 410 nm produces a strong beam with sufficient photons to permit the formation of the visible spot 38 on the tissue being examined. Being able to see the spot is crucial to being able to point the hand-held, self contained instrument, which is intended for use by a physician in-vivo while examining a patient, directly and with certainty toward the intended target area. Similarly, by allowing sufficiently large wavebands of emitted fluorescent light to reach the light sensor 44, the signals are less susceptible to errors due to system noise.

According to another aspect of the invention, I found that all the information contained within a certain range of emitted fluorescent wavelengths, rather than only selected narrow wavebands, can be used to differentiate the response of cancerous cells from that of healthy ones. A comparison of the fluorescent spectra emitted by diseased and healthy cells of different kinds of tissue reveals that a much more pronounced difference exists below a certain demarkation wavelength, which is characteristic of the type of cell, than above that wavelength. For the purposes of this disclosure, such wavelength is defined as a "demarkation wavelength" to indicate the wavelength that separates a region of substantial similarity from one of marked dissimilarity between the spectra of healthy and cancerous cells. It is noted that certain types of tissue may exhibit more than one demarkation wavelength separating multiple regions of substantial similarities and dissimilarities.

Figure 2:
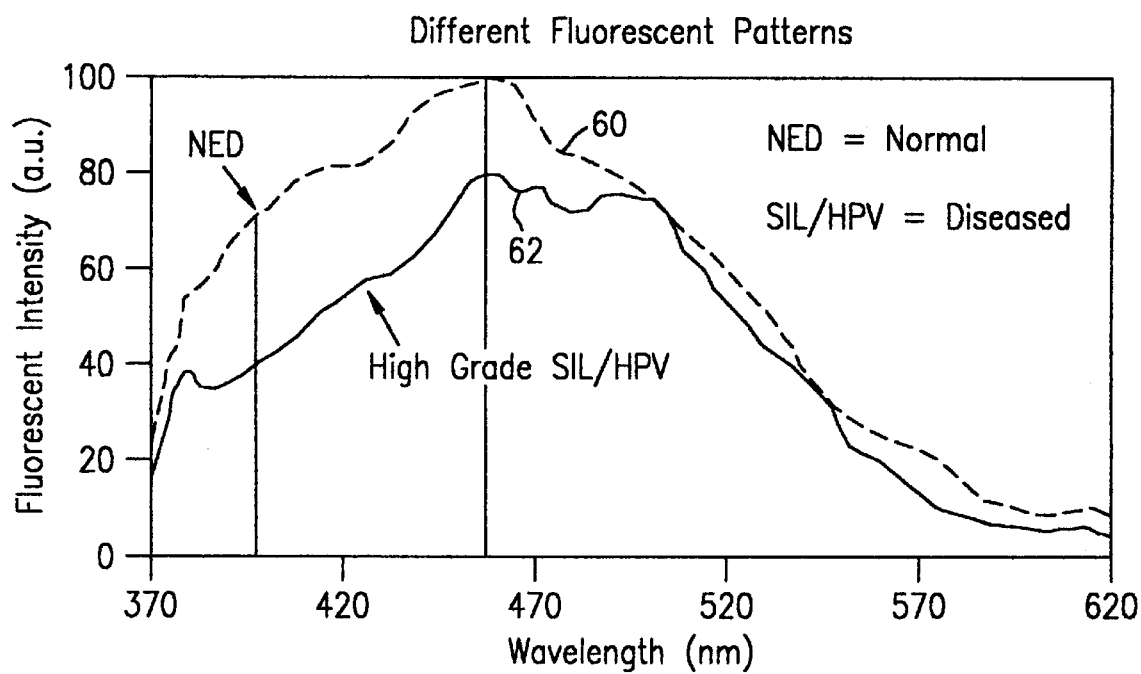
FIG. 2 is an illustration of fluorescent emission spectra obtained from a normal and a diseased tissue.

In some cases the regions of similarity and dissimilarity are not well defined, but are very subtle. For example, FIG. 2 illustrates the fluorescent emissions of cancerous and healthy cells excited by a light. The spectral response of normal tissue is represented by curve 60, while the response of cancerous tissue is shown as curve 62. It is clear that the two curves are significantly different at wavelengths shorter than about 500 nm, but are substantially the same above that wavelength. This property is exploited in this invention by identifying 500 nm as the demarkation wavelength and by selecting fluorescent emission wavebands below and above this 500 nm threshold for analysis, such as, for example, from 415 to 460 and from 500 to 620 nm. As illustrated in the figure, the normal and diseased curves are substantially the same from 500 to 620 nm. However, in the shorter spectral region, the fluorescent intensity of the normal curve integrated over the test waveband (415–460 nm) is approximately 1.5 times that of the diseased curve, on average. Thus, in the absence of background noise, any ratio below about 1.3 could be used reliably to indicate normality for this type of tissue. This test costitutes the simplest form of an algorithm to carry out the invention.

It is noted that the fluorescent emission of normal tissue is not always higher than that of abnormal tissue. Often the opposite occurs, but it appears that in all instances a demarkation wavelength exists that enables the practice of this invention. The fluorescent emission bands used for each particular application are selected on the basis of clinical testing and detailed spectral data for the type of tissue being examined. These spectra are preferably developed using a spectral resolution of approximately 1 nm. The emission spectrum of healthy tissue of the type being examined can be recorded in the microprocessor 46 as a reference data curve available for comparison with fluorescent intensities measured in-vivo from the tissue under examination. Alternatively, a normal fluorescent-intensity reading for each frequency band can be obtained in-vivo from a patient under examination by shining the instrument 10 on an area of healthy tissue near the target, so that the normal value is obtained currently for comparison with the test value emitted by the tested surface.

The procedure of the invention can be implemented using information from as few as two frequency bands, one below and the other above the demarkation wavelength for the particular tissue of interest (as discussed above). For more discriminating results, though, a variety of ratios can be used that provide different levels of diagnostic certainty. In fact, I found that two well selected bands could discriminate completely cancerous from normal cells even though the spectra did not look different to the eye.

In principle, the first point underlying the idea of the invention is to utilize ratios of the fluorescence intensity of the normal (reference) tissue to that of the tissue being tested (or vice versa) for each waveband available, rather than taking the ratio of intensities at two predetermined wavelengths (as disclosed by Alfano et al.). These ratios are then compared and variations (which may be measured by their ratio) are used to determine a cancerous condition. The process is carried out for each type of tissue intended to be tested by first identifying the wavelength region where the normal and diseased spectra of the emitted fluorescent light are substantially similar (i.e., defining the demarkation wavelength). Then, multiple wavebands, preferably at least 45-nm wide, are selected in that region as well as in the wavelength region where diseased spectra are known to diverge and are used for testing purposes. Measurements of fluorescent-emission intensity in these wavebands are then judiciously utilized to identify abnormal tissue by comparing ratios in a manner that leads to a meaningful discrimination between the normal and the diseased spectra. It is noted that only fluorescent wavebands substantially above the wavelength of the excitation light, at least 10 nm greater (preferably 40 nm), appear to be acceptable for this purpose. The spectral interval depends upon the quality of the filter that is used. The reflected excitation light must not be allowed to contaminate the emitted fluorescence.

The process by which spectral bands can best be chosen to distinguish diseased from healthy tissue may be illustrated with reference to a system that uses only two bands. If R1 is the ratio of the fluorescent intensities (measured by the integrated product of the spectral flux times the system spectral responsivity) of the test to the reference tissue in the first band, and R2 is the equivalent ratio in the second band, then one wishes to maximize the ratio of R1 to R2 as a function of bandwidth limits. This can be done by multiplying the spectral data with the responsivity point-by-point and summing the products between different spectral limits. Systematic variations of the waveband boundaries are then carried out. Since a wider band means a better signal-to-noise ratio and lower uncertainty, the optimization can be performed with contraints on the flux times responsivity integral that ensure an acceptable signal-to-noise ratio. The limits of both wavebands are adjusted point by point to give the greatest ratio (R1/R2) subject to the condition that neither bandwidth becomes smaller than a chosen value, which, as those skilled in the art readily understand, can be determined by a radiometric signal analysis based on the power of the illumination, the efficiency of the fluorescence, the optical transmission of the unit, the sensitivity of the detector and the performance of the electronics. Limits for the wavebands below and above the demarkation wavelength can thus be determined. It is noted that reverse ratios of those described could be used in equivalent fashion in the procedsure, so long as consistently applied.

Figure 3:
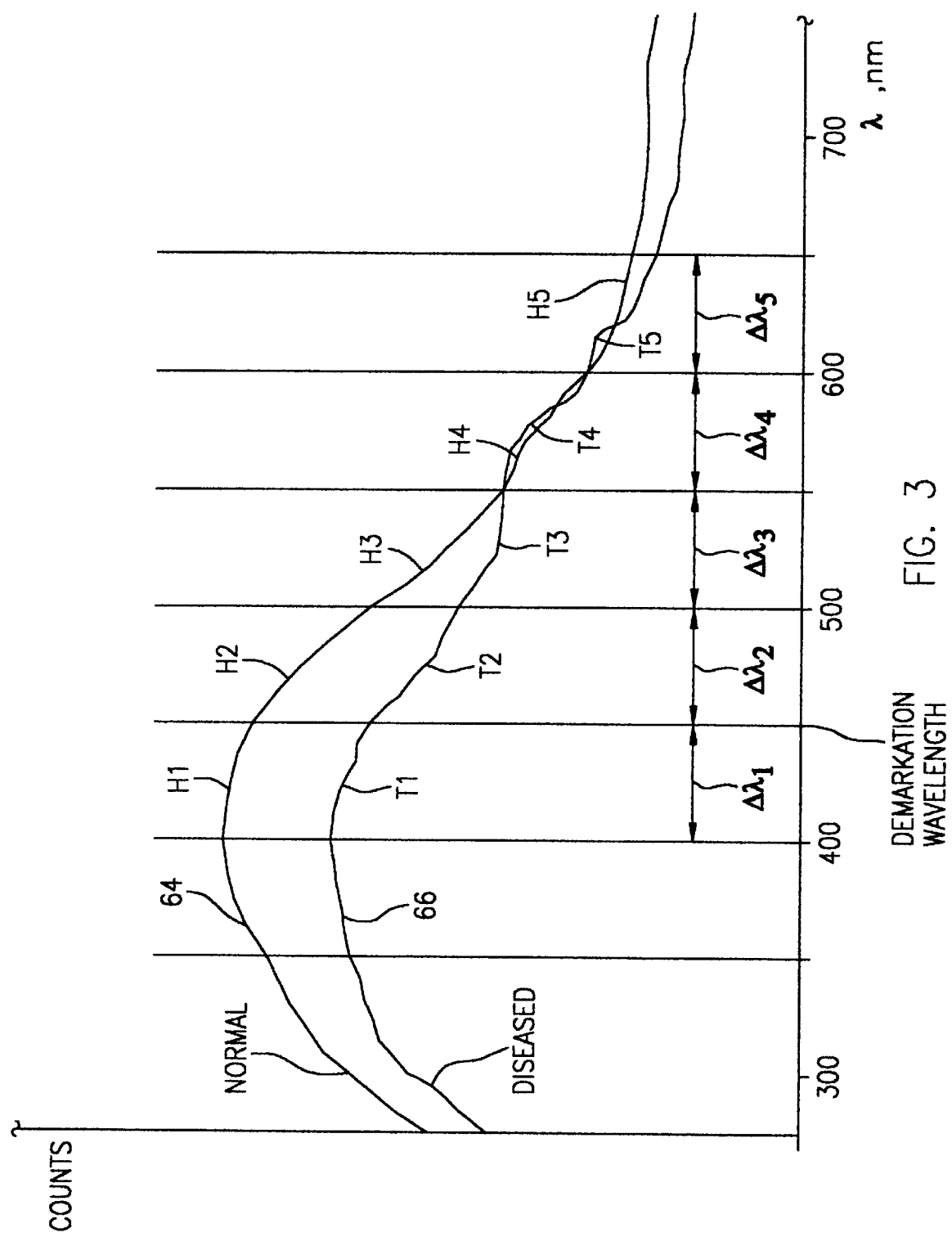
FIG. 3 is a graphic illustration of the utilization of fluorescent emission spectra to differentiate between diseased and normal tissue.

As a practical example, defining H1, H2, H3, etc. as the emission intensities of healthy tissue corresponding to progressively longer wavebands $\Delta\lambda 1$, $\Delta\lambda 2$, $\Delta\lambda 3$, etc., respectively, and T1, T2, T3, etc. as the emission intensities of tissue being tested at the same wavelengths $\Delta\lambda 1$, $\Delta\lambda 2$, $\Delta\lambda 3$, etc., the invention may be practiced by comparing ratios of intensities corresponding to each waveband, i.e. T1/H1, T2/H2, T3/H3, (=R1, R2, R3,) etc. For instance, FIG. 3 shows a curve 64 for a normal tissue spectrum and a curve 66 for the tested tissue spectrum, with segments H1 and T1 being emission readings obtained during the test at $\Delta\lambda 1=$ 400–450 nm, $\Delta\lambda 2=$450–500, etc. at consecutive 50-nm intervals. The curves define a region where the intensity spectra are substantially equal (essentially above 550 nm, the demarkation wavelength for this particular type of tissue). According to the invention, a first level of differentiation is obtained by a comparison of H1/T1 and H4/T4 which, as illustrated with respect to FIG. 2, would indicate normality when the deviation between H1/T1 and H4/T4 (which deviation may be measured by their ratio) is less than a predetermined threshold factor empirically judged to be significant for the purpose of discriminating between healthy and normal cells.

If the spectra of healthy and abnormal tissue are sufficiently alike, the differentiation can be obtained by using ratios of intensity data from other wavebands as well, such as R2, R3 and R5, and comparing the values of such ratios in these other regions below and above the demarkation wavelength of about 550 nm. These additional checks can also be used to confirm the consistency of the various frequency regions below and above the demarkation wavelength.

It must be realized that the ratio of the outputs in these bands is a function not only of the fluorescent spectra of the sample, but also the spectral responsivity of the detector that is being used. The threshold factors that are established to compare intensity ratios must therefore also depend upon the detector, which in the preferred embodiment is silicon, known to have substantially constant response to photon flux and linearly increasing response to power. Thus, as one skilled in the art would readily understand, each ratio is really given by the following expression $$\text{Ratio} = \frac{\int_{\Delta\lambda} R_H(\lambda) I_H(\lambda) d\lambda}{\int_{\Delta\lambda} R_T(\lambda) I_T(\lambda) d\lambda} \qquad (1)$$

where $\lambda$ it the wavelength of the fluorescent emission; $\Delta\lambda$ is the measured waveband; $R(\lambda)$ is the responsivity of the system; $I(\lambda)$ is the light intensity; and the subscripts H and T refer to healthy and test tissues, respectively.

Figure 4:
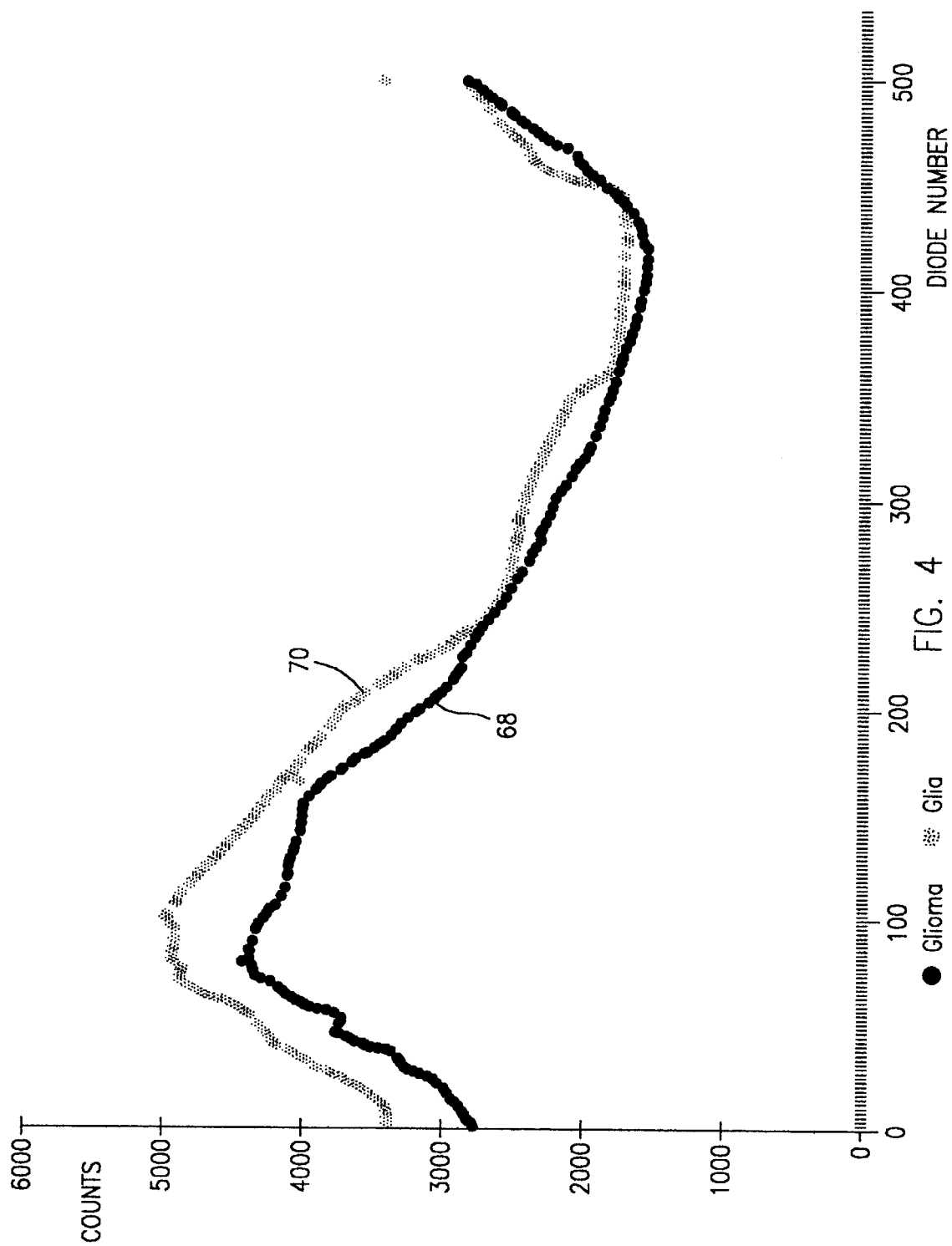
FIG. 4 is a plot of superimposed fluorescent emission spectra of glia and glioma cells illustrating the diagnostic identification procedure of the invention.
Figure 5:
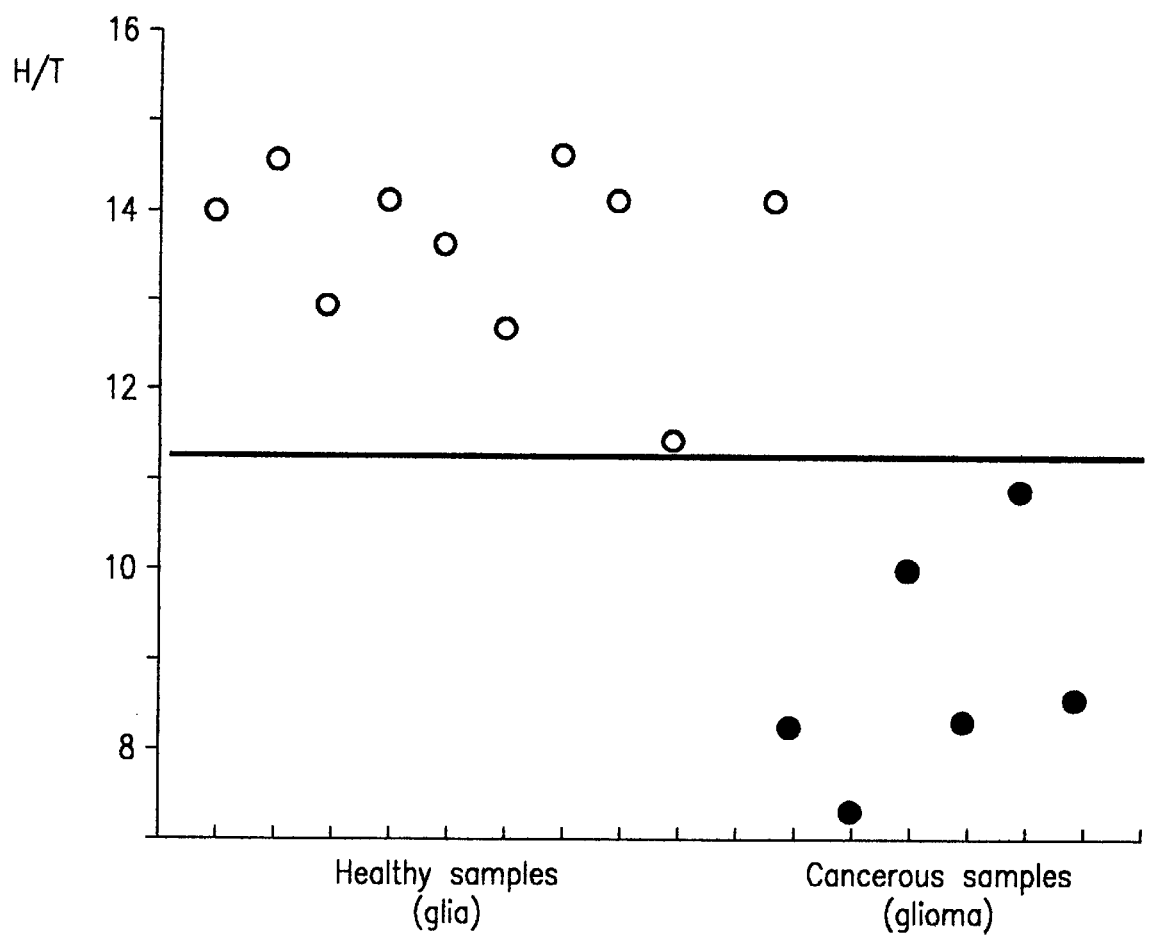
FIG. 5 is a plot showing the results of various diagnostic tests utilizing the procedure of the invention to distinguish diseased tissue from healthy tissue.

FIGS. 4 and 5 illustrate the results obtained from an examination of healthy (glia) and cancerous (glioma) samples of nerve tissue. FIG. 4 shows the fluorescence spectrum 68 of healthy glia cells superimposed over the spectrum 70 obtained from cancerous glioma cells. FIG. 5 illustrates fluorescent-emission ratios data points of healthy and cancerous cells separated by an arbitrary threshold value of about 11 found to be valid for discrimination purposes.

In the preferred embodiment of the invention, the light source 20 (see FIG. 1) is a xenon arc lamp with a mirror behind it to help direct the excitation light, but it could be a tungsten halogen bulb, a mercury arc lamp, a Xe-Hg arc lamp or other appropriate source with sufficient radiation in the specified band. The source is filtered with an interference filter that passes light in the part of the spectrum from approximately 370 to approximately 410 nm. The preferred central wavelength is 370 nm. The lens 28 collimates the energy from the source, thereby relaxing the tolerances for placement of the other optical components and providing collimated light to the field-defining aperture system, which consists of lenses 32,36 and the adjustable iris 34. The beamsplitter 30 is preferably bichromatic; that is, it reflects light substantially in the region from approximately 370 to approximately 410 nm and transmits light substantially from about 450 to about 700 nm. The adjustable-aperture system defines the field of view both for illumination and reception, thereby obtaining co-alignment to ensure that the desired target area, such as a lesion in a patient, and only the target area is illuminated and sensed. The fluorescent light returned to the instrument passes back through the beamsplitter 30 to the filter set 42 and detector 44. The filter set 42 comprises a number of filters of different wavebands, such as, for example, 415 to 460 nm, 460 to 500 nm, and 500 to 620 nm, which may be accomplished with interference, absorption, reststrahlen filters, or any combination of them. The signals from each of the filters in set 42 are sequentially sent to the microprocessor 46 where the algorithms for discrimination are applied. A decision is made by the microprocessor, and the result is presented on the display unit 48.

In operation, a user holds the device an appropriate distance from the surface to be tested (~5 to ~20 inches) and presses the trigger 18 half way. This turns on the light source 20 and a spot 38 is shone on the surface. The size of the spot 38 is adjusted, if necessary, by actuating trigger 16, which is a toggle switch. This switch actuates the motor 52, which opens or closes the iris 34. When the spot reaches the desired size and is in the right position, the trigger 18 is squeezed all the way for a reading. Then, in sequence, a signal is obtained with each of the filters in the set 42 by continuing squeezing trigger 18. The signals are then processed and the display generated. Once the trigger 18 is fully pressed, the sequence proceeds automatically and is over in a few seconds. The process can be repeated on the same or other lesions. This procedure applies for a system where the normal fluorescence emission spectrum has been stored in memory. For systems where comparison information need to be obtained currently from a healthy portion of the tissue, an appropriate switch would be provided to select the operation mode for data collection as needed to apply a discrimination algorithm according to the invention. Inasmuch as such design feature would be obvious to one skilled in the art, it will not be detailed here.

In order to produce a lighter instrument, or one with more data-storage capability, only the optical system components could be incorporated in the portable case of the invention. The power could be supplied from properly processed outlet current and delivered through a cable. Similarly, the detector output signals could be carried through separate, properly shielded wires in the same cable to a display in a separate console equipped with computer memory and storage capabilities.

The filter set 42 can comprise from 2 to 5 different filters, depending on the number of wavebands required by the selection algorithm utilized in the system. For simplicity, the preferred embodiment has only 2. In each case the wavebands are determined by laboratory or prior clinical investigation of appropriate cells.

Figure 6:
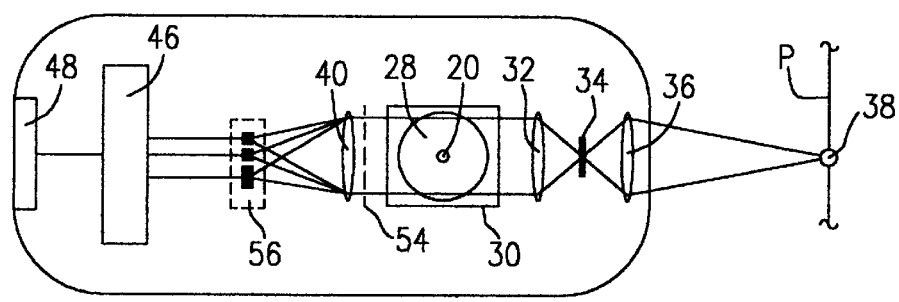
FIG. 6 is a schematic, plan view of another embodiment of a manually-operated detection instrument according to the invention, wherein a grating unit is used instead of multiple filters.

In an equivalent embodiment of the apparatus of the invention, illustrated in plan view in FIG. 6, the filter set 42 of the first embodiment is replaced with a single grating 54. In this embodiment, from 2 to 5 individual detectors 56 can be used, corresponding to the optical properties of the grating 54. Alternatively, an acousto-optical or electro-optical filter may be used in the same sequential manner with a single detector. In still another alternative embodiment, a prism rather than a grating may be used in this configuration.

Figure 7:
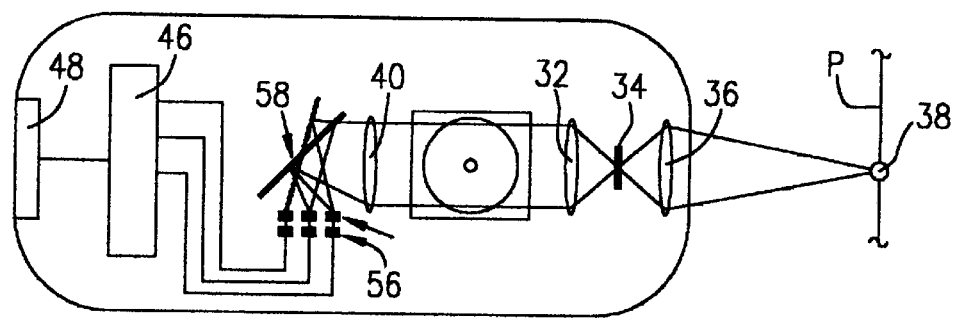
FIG. 7 is a schematic, plan view of another embodiment of a manually-operated detection instrument according to the invention, wherein a scanning mirror that can take multiple positions to focus light onto individual detectors is used instead of multiple movable filters.

The arrangement may also include an array of detectors 56 with a scanning mirror as shown in FIG. 7, wherein all the components are the same as in FIG. 6 with the exception of element 58, which is a scanning mirror that can take on from 2 to 5 different positions to focus light onto the individual detectors through their respective, fixed filters 43.

In all embodiments, sequential signals from the detector arrays are sent to the microprocessor wherein the algorithms for discrimination are applied. A decision is made by the microprocessor, and the result is presented on the display unit. The sensor array used for the invention is a typical silicon array, such as that used in camcorders. It consists of approximately 500×500 pixels. It is noted that the optical system is designed such that each pixel corresponds approximately to the size of a tissue cell in order to maximize the contrast between normal and malignant tissue.

Thus, the spectral signals generated with each of the different filters are processed for each pixel. The image so generated is preferably in false colors, possibly red for cancers, yellow for neoplasia and green or blue for normal tissue. In all of these configurations, light in a band in the spectral region from approximately 370 nm to approximately 410 nm is caused to illuminate the tissue in question. The tissue, in turn, fluoresces naturally rather than through the influence of drugs, as done in some prior-art practice. The spectrum of the fluorescent light is analyzed to determine its chemical and biological state. Also in contrast with previous practice, in which several illumination bands, light pulses and spectrometers are used with more than 100 analysis bands of the return fluorescence, this invention accomplishes the discrimination with as few as two bands. These bands have no necessary relationship to blood absorption bands.

Figure 8:
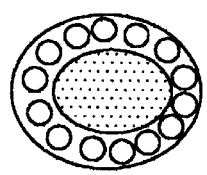
FIG. 8 is a schematic, plan view of an embodiment of the instrument of the invention including a fiber-optics bundle for testing interior body tissue.
Figure 8:
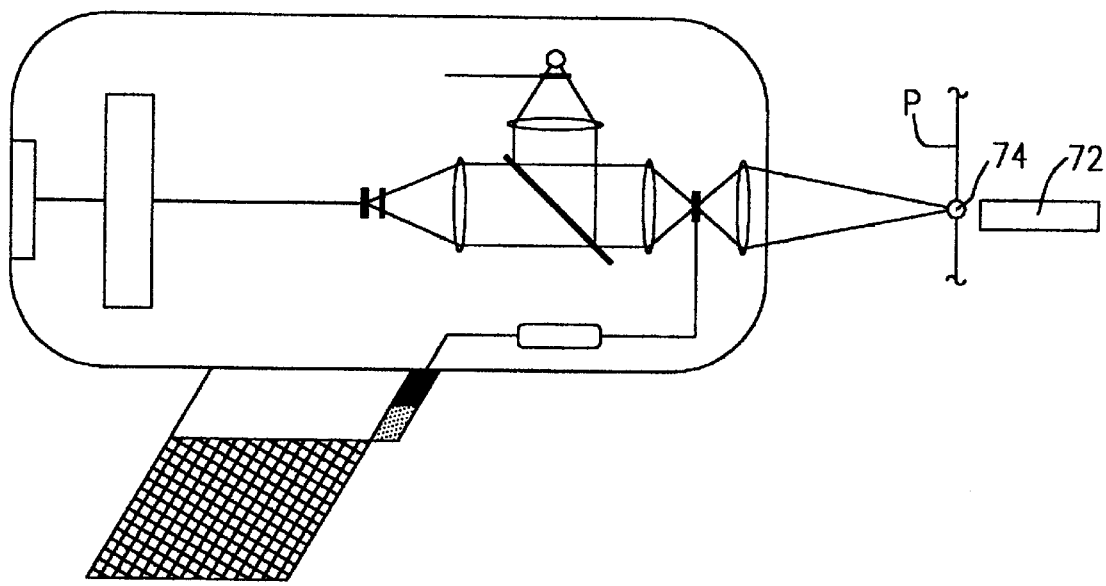

It should be obvious to one skilled in the art that there are other, similar techniques that may be employed. For instance, one could use any relatively wide band for illumination as long as it provides distinguishing fluorescent spectra. One need not use continuous radiation but could use pulses. One could permit overlapping of the illumination spectra and fluorescent spectra, if they were then distinguished by such techniques as different modes of modulation. One can also use overlapping reception bands with proper processing. One could use fiber optics to reach otherwise inaccessible areas, as illustrated in the device of FIG. 8, where the fiber-optics bundle 72 is used to feed the excitation light from, as well as to return the fluorescence light to, a focal point 74 on a patient P.

It should also be obvious that, with appropriate designs of the optical systems, this invention can be applied to the discrimination of skin cancers, cervical cancer, esophageal cancer, rectal cancer, prostate cancer, lung cancer and others. For applications in which the surface tissue is not directly visible to the clinician, the optical system would "feed" the light to an appropriate fiber optic probe. Some of the fibers would conduct the excitation light to the area to be diagnosed, while others would return the fluorescence light to the detector and filter system.

The instrument can also be used to evaluate exfoliated tissue, such as that taken from the cervical area, as in the first steps of a Papinicolau, "Pap" smear. In this case, however, the tissue is spread thinly on a slide and is illuminated with violet or ultraviolet light. A large region of the slide is imaged and the process applied to each pixel in the image. A further application is the use of the instrument on samples that have been taken from spinal taps, involving, for example, glia and glioma cells.

Various changes in the details, steps and components that have been described may be made by those skilled in the art within the principles and scope of the invention herein illustrated and defined in the appended claims. Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent processes and devices.

I claim:

1. A method for diagnosing an abnormal condition in a tissue under examination, comprising the following steps:
    (a) illuminating a normal tissue with an excitation light having a bandwidth sufficient to form a visible spot thereon;
    (b) filtering a fluorescent light emitted from said normal tissue in response to step (a) to provide at least two wavebands of normal fluorescence, each waveband being at least about 45 nm wide;
    (c) measuring an intensity of normal fluorescence for each said waveband produced in step (b);
    (d) repeating steps (a) through (c) for a test tissue being examined for abnormality, thereby measuring an intensity of test fluorescence corresponding to said test tissue for each said waveband;
    (e) calculating a ratio of said intensity of normal fluorescence to said intensity of test fluorescence for each said waveband; and
    (f) comparing the ratios so calculated to discern dissimilarities indicative of an abnormal condition in the test tissue.

2. The method of claim 1, wherein said abnormal condition in a tissue is an indication of a presence of cancerous cells, and said wavebands are selected in a wavelength range between 450 and 700 nm.

3. The method of claim 2, wherein said excitation light has a waveband in the range between 370 and 410 nm.

4. The method of claim 1, wherein said filtering step is carried out using a set of filters selected from the group consisting of interference filters, absorption filters, acousto-optical filters, electro-optical filters, reststrahlen filters, or any combination thereof.

5. The method of claim 1, wherein said filtering step is carried out using a grating.

6. The method of claim 1, wherein said filtering step is carried out using a prism.

7. The method of claim 1, wherein said bandwidth of the excitation light is approximately 40 nm and is separated from said wavebands of fluorescent light by at least 10 nm.

8. The method of claim 1, wherein said at least two wavebands consist of two to five wavebands in a wavelength range between 450 and 700 nm.

9. An optical device for detecting cancerous tissue, comprising:
    means for focusing an excitation light beam on a tissue to form a visible spot thereon;
    means for detecting a fluorescent light emitted from said tissue in a plurality of wavebands, each waveband being at least 45 nm wide; wherein said detection means is operable to produce an intensity of normal fluorescence from a normal tissue and an intensity of test fluorescence from a test tissue;
    means for calculating a ratio of said intensity of normal fluorescence to said intensity of test fluorescence for each said waveband; and
    means for comparing the ratios so calculated to discern dissimilarities indicative of a cancerous condition in the test tissue.

10. The device of claim 9, wherein said excitation light beam has a bandwidth of approximately 40 nm and is separated from said wavebands of fluorescent light by at least 10 nm.

11. The device of claim 9, wherein said plurality of wavebands is produced by a filter system in a wavelength range between 450 and 700 nm.

12. The device of claim 11, wherein said excitation light beam has a waveband in the range between 370 and 410 nm.

13. The device of claim 11, wherein said filter system comprises a set of filters selected from the group consisting of interference filters, absorption filters, acousto-optical filters, electro-optical filters, reststrahlen filters, or any combination thereof.

14. The device of claim 11, wherein said filter system comprises a grating.

15. The device of claim 11, wherein said filter system comprises a prism.

* * * * *